United States Patent
Yada et al.

(10) Patent No.: US 9,557,261 B2
(45) Date of Patent: Jan. 31, 2017

(54) SPECTROSCOPIC ANALYSIS METHOD AND SPECTROSCOPIC ANALYZER

(71) Applicant: HORIBA, Ltd., Kyoto-shi, Kyoto (JP)

(72) Inventors: Takaaki Yada, Kyoto (JP); Shun Kuroda, Kyoto (JP); Issei Yokoyama, Kyoto (JP); So Takagi, Kyoto (JP); Yoko Nakai, Kyoto (JP)

(73) Assignee: HORIBA, Ltd., Kyoto-shi (JP)

( * ) Notice: Subject to any disclaimer, the term of this patent is extended or adjusted under 35 U.S.C. 154(b) by 371 days.

(21) Appl. No.: 14/141,324

(22) Filed: Dec. 26, 2013

(65) Prior Publication Data

US 2014/0185049 A1    Jul. 3, 2014

(30) Foreign Application Priority Data

Dec. 27, 2012  (JP) ................. 2012-285524

(51) Int. Cl.
*G01N 21/27*    (2006.01)
*G01N 21/31*    (2006.01)

(52) U.S. Cl.
CPC .......... *G01N 21/274* (2013.01); *G01N 21/314* (2013.01)

(58) Field of Classification Search
CPC ............................ G01N 21/274; G01N 21/314
See application file for complete search history.

(56) References Cited

U.S. PATENT DOCUMENTS 3,975,727 A * 8/1976 Mader .................. G01N 21/274
                                                                341/140

5,386,295 A * 1/1995 Switalski ................. G01J 3/02
                                                                250/458.1

(Continued)

FOREIGN PATENT DOCUMENTS

EP    1785719 A1    5/2007
JP    03024438 A    2/1991
(Continued)

OTHER PUBLICATIONS

English machine translation of JP 2002082050 A, Yokoyama, Mar. 2002.*

(Continued)

*Primary Examiner* — Kara E Geisel
*Assistant Examiner* — Dominic J Bologna
(74) *Attorney, Agent, or Firm* — Alleman Hall McCoy Russell & Tuttle LLP (57) ABSTRACT

The present invention improves an S/N ratio and light intensity resolution provided by an A/D converter, and an analyzer includes: a measurement cell irradiated with light during sample measurement; a dimming element irradiated with the light during reference measurement; an amplifier configured to amplify an analog light intensity signal outputted from a light detector; an A/D converter configured to convert the analog light intensity signal into a digital light intensity signal; and an arithmetic device configured to calculate absorbance using a digital sample light intensity signal outputted from the A/D converter during the sample measurement and a digital reference light intensity signal outputted from the A/D converter during the reference measurement, wherein an amplification factor of the amplifier is set such that the analog reference light intensity signal and the analog sample light intensity signal become less than or equal to a full scale of the A/D converter.

3 Claims, 9 Drawing Sheets

(56) References Cited

U.S. PATENT DOCUMENTS

| | | | | |
|---|---|---|---|---|
| 5,526,121 A * | 6/1996 | Sandifer | ............... | G01J 3/02 |
| | | | | 250/351 |
| 2010/0182605 A1 * | 7/2010 | Stockwell | ............ | G01J 3/12 |
| | | | | 356/436 |

FOREIGN PATENT DOCUMENTS

| | | | |
|---|---|---|---|
| JP | 2000275172 A | 10/2000 | |
| JP | 2002082050 A | 3/2002 | |
| JP | 2005037294 A | 2/2005 | |
| JP | 2012137303 A | 7/2012 | |
| WO | 2006025104 A1 | 3/2006 | |

OTHER PUBLICATIONS

Japanese Patent Office, Office Action Issued in Japanese Patent Application No. 2012-285524, May 7, 2015, 3 pages.

* cited by examiner

(PRIOR ART)

SPECTROSCOPIC ANALYSIS METHOD AND SPECTROSCOPIC ANALYZER

TECHNICAL FIELD

The present invention relates to a spectroscopic analysis method and a spectroscopic analyzer for measuring absorbance of a liquid sample.

BACKGROUND ART

Figure 9:
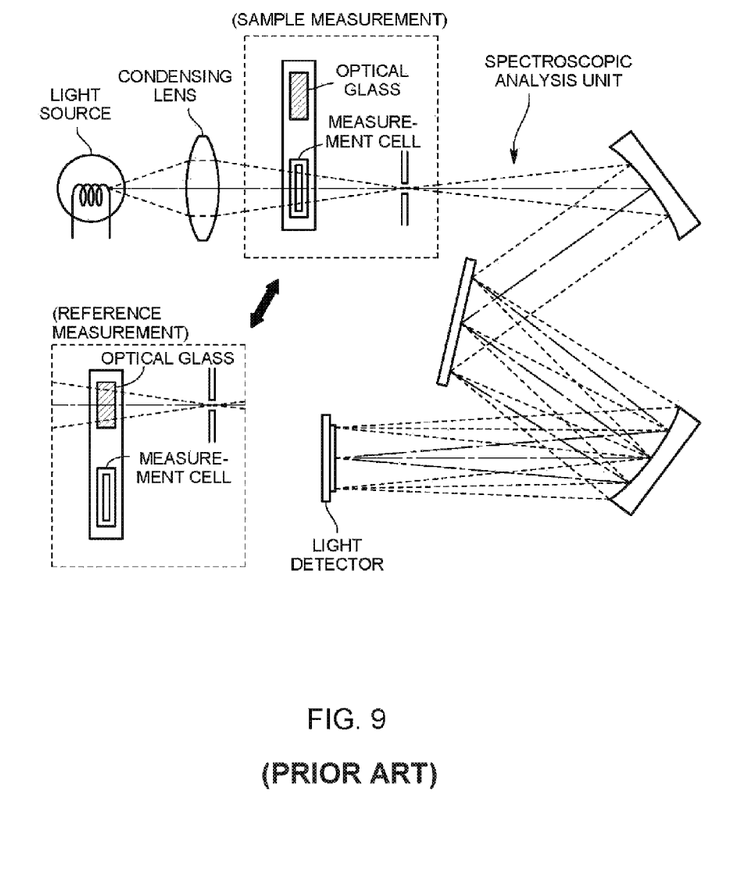
FIG. 9 is a schematic diagram showing configuration of the conventional spectroscopic analyzer.

There is a conventional spectroscopic analyzer which includes: as shown in Patent Literature 1, a light source; a condensing lens condensing light from this light source; a spectroscopic analysis unit having a multi-channel detector (light detector) and which performs spectroscopic analysis of the light from the light source; and a measurement cell being arranged between the condensing lens and the spectroscopic analysis unit (see FIG. 9).

An absorption spectroscopy method is used for concentration measurement in this spectroscopic analyzer. Typically, in this absorption spectroscopy method, concentration cj is typically calculated by multiplying an absorbance spectrum Abs ($\lambda i$) by a calibration curve Mij previously obtained through calibration (see equation below). $\lambda 1, \lambda 2, \ldots \lambda n$ are measurement wavelengths and cj is concentration of the j-th component.

[Equation 1]

$$cj = \sum_{i=1}^{n} Mij \times \text{Abs}(\lambda i) \quad \text{(Equation 1)}$$

The absorbance spectrum Abs ($\lambda i$) can be expressed by the following equation based on intensity $I_0$ ($\lambda i$) of light entering the measurement cell and intensity Is ($\lambda i$) of light transmitted through the measurement cell.

[Equation 2]

$$\text{Abs}(\lambda i) = \log \frac{I_0(\lambda i)}{I_S(\lambda i)} \quad \text{(Equation 2)}$$

Here, it is difficult to directly measure the intensity $I_0$ ($\lambda i$) of the entering light, and with the conventional spectroscopic analyzer, in a state in which a measurement lens is removed from between the condensing lens and the spectroscopic analysis unit (reference measurement), intensity of light measured by the spectroscopic analysis unit, that is, intensity $I_R$ ($\lambda i$) of reference light is substituted. That is, with the following equation, the absorbance spectrum Abs ($\lambda i$) is obtained. In the spectroscopic analyzer of Patent Literature 1, optical glass of, for example, quartz is arranged for the purpose of correcting a change in a focal position caused by the presence or absence of the measurement cell on a light path (see FIG. 9).

[Equation 3]

$$\text{Abs}(\lambda i) = \log \frac{I_R(\lambda i)}{I_S(\lambda i)} \quad \text{(Equation 3)}$$

Moreover, with the spectroscopic analyzer of this kind, a measurement wavelength and a light path length of the measurement cell are typically set so that absorbance when a liquid sample is stored in the measurement cell becomes approximately 1 Abs to 2 Abs (transmittance of approximately 10% to 1%) where absorbance reference (an absorbance of zero) is provided for the case where air is stored in the measurement cell. This is because for an absorbance of 1 or below (transmittance of 10% or above), absorbance variation corresponding to concentration variation of the liquid sample is small and thus concentration measurement cannot be performed with high accuracy. On the other hand, for an absorbance of 2 or above (transmittance of 1% or below), an intensity of transmitted light is small and thus it is difficult to perform accurate light intensity measurement and also perform concentration measurement with high accuracy.

Figure 2:
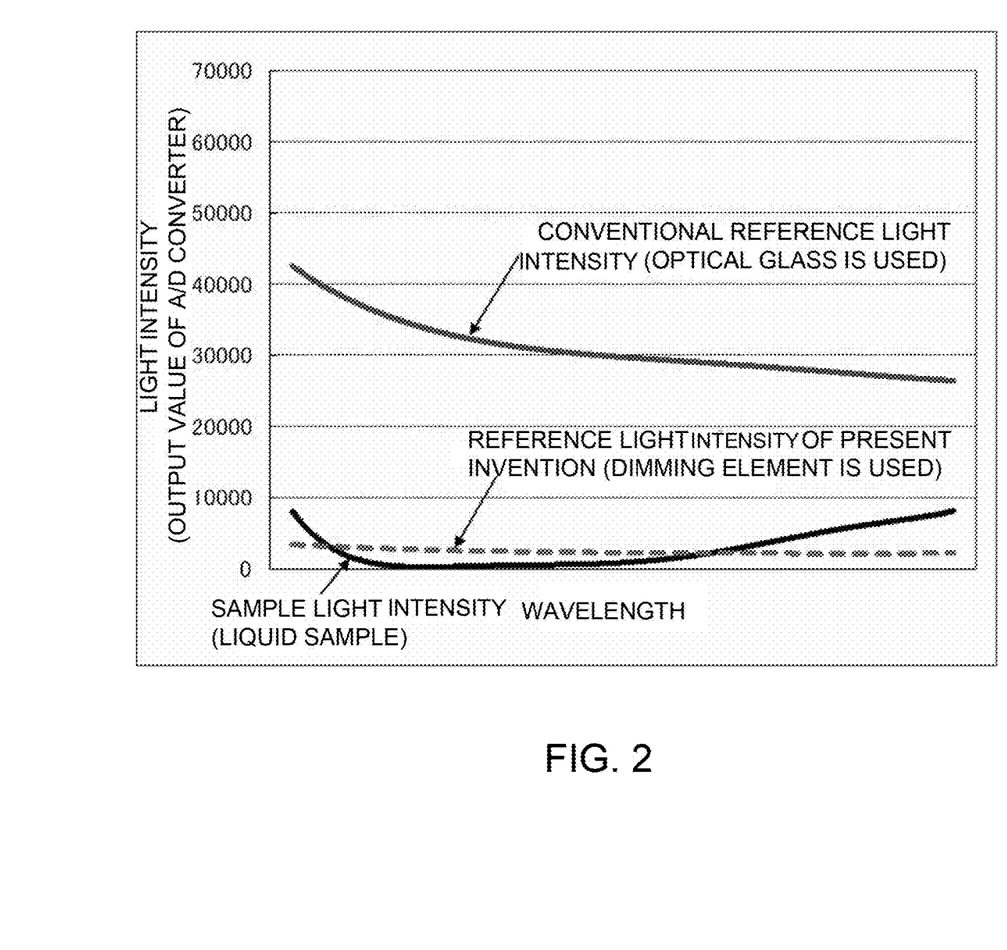
FIG. 2 is a diagram showing light intensity signals obtained by an A/D converter in a conventional spectroscopic analyzer.

However, transmittance of optical glass used for the reference measurement is approximately 90%, and thus a ratio of intensity of the reference light (an output value of an analog-to-digital [A/D] converter) with respect to intensity of the sample light (an output value of the A/D converter) becomes approximately ten times to hundreds of times as shown in FIG. 2. The sample light and the reference light are detected by the same optical detector, and their light intensity signals are amplified by the same amplifier and are converted by the same A/D converter, and thus as a result of a large difference in light intensity signals between the sample light intensity and the reference light intensity, disadvantages arise in both the signal-to-noise (S/N) ratio and the light intensity resolution.

Specifically, since the intensity of the sample light is small, the light intensity signal outputted from the optical detector is small, deteriorating the S/N ratio due to an influence from disturbance noise such as electromagnetic noise. Moreover, a full scale of the A/D converter is set in accordance with the reference light with large intensity, and thus the sample light with small intensity needs to be subjected to A/D conversion within a narrow range of the A/D converter. This means that the intensity of the sample light needs to be measured with a rough bit, and light intensity resolution provided by the A/D converter decreases.

CITATION LIST

Patent Literature

Patent Literature 1: JP-A 2002-82050

SUMMARY OF INVENTION

Technical Problem

To solve the problem described above, the present invention has been made, and it is a main object of the present invention to improve an S/N ratio and also improve light intensity resolution provided by an A/D converter.

Solution to Problem

Specifically, a spectroscopic analyzer corresponding to one aspect of the present invention includes: a light source; a measurement cell storing a liquid sample irradiated with light of the light source during sample measurement; a dimming element being irradiated with the light of the light source during reference measurement; a light detector configured to detect sample light which has passed through the measurement cell and configured to detect reference light which has passed through the dimming element during reference measurement; an amplifier configured to amplify an analog sample light intensity signal as outputted from the light detector during sample measurement and configured to amplify an analog reference light intensity signal outputted from the light detector during reference measurement; an A/D converter configured to convert the analog sample light intensity signal into a digital sample light intensity signal and configured to amplify the analog reference light intensity signal into a digital reference light intensity signal; and an arithmetic device configured to calculate an absorbance of the liquid sample using the digital sample light intensity signal outputted from the A/D converter during the sample measurement and the digital reference light intensity signal outputted from the A/D converter during the reference measurement, wherein the analog sample light intensity signal and analog reference light intensity signal inputted to the A/D converter are amplified in a manner such that the digital reference light intensity signal and the digital sample light intensity signal become less than or equal to a full scale of the A/D converter.

According to another aspect of the present invention, a spectroscopic analysis method arranges, between a light source and a light detector, a measurement cell storing a liquid sample to acquire an analog sample light intensity signal, arranges a dimming element to acquire an analog reference light intensity signal, and calculates absorbance by using a digital sample light intensity signal and a digital reference light intensity signal, and the digital sample light intensity signal and the digital reference light intensity signal are obtained by amplifying, by use of an amplifier, an analog sample light intensity signal of sample light and an analog reference light intensity signal of reference light detected by the light detector and converting the analog sample light intensity signal into a digital sample light intensity signal and a digital reference light intensity signal by an A/D converter, and the analog sample light intensity signal and the analog reference light intensity signal inputted to the A/D converter are amplified in a manner such that the analog reference light intensity signal and the analog sample light intensity signal become less than or equal to a full scale of the A/D converter.

Here, as a method of amplifying the analog signals inputted to the A/D converter, it is possible to set the amplification factor of the amplifier so that the reference light intensity signal and the sample light intensity signal become less than or equal to the full scale of the A/D converter. In addition, it is possible to increase a resistance value of an output resistor provided at the light detector and convert a current value generated by the light detector into a voltage value by the output resistor to thereby increase a light intensity signal composed of the voltage value.

With the configuration as described above, since the dimming element is used in the reference measurement, the light intensity signal of the light which has passed through the dimming element during the reference measurement can be intentionally decreased to be thereby equalized with the light intensity signal of the light which has passed through the measurement cell during the sample measurement.

Then since the amplification factor of the amplifier is set so that the reference light intensity signal and the sample light intensity signal become less than or equal to the full scale of the A/D converter, both the reference light intensity signal and the sample light intensity signal can be increased to such degrees that do not exceed the full scale of the A/D converter.

Therefore, the light intensity signal obtained during the sample measurement can be amplified more than in the conventional case, thus improving an SIN ratio for disturbance noise such as electromagnetic noise. Moreover, the sample light intensity signal can be increased to such a degree that does not exceed the full scale of the A/D converter, thus improving light intensity resolution in the A/D converter. As a result of the above, accurate light intensity measurement is possible, permitting concentration measurement with high accuracy.

Here, the amplification factor of the amplifier is set at a value that exceeds the full scale of the A/D converter and goes off the scale as a result of subjecting the light intensity signal outputted from the light detector to A/D conversion by the A/D converter, in the case where reference measurement is performed without using the dimming element.

It is desirable that the dimming element be an optical filter. Here, the optical filter is formed of a solid material which absorbs a specific wavelength. The optical filter encounters only minor temperature variation and does not necessarily require temperature correction, which can therefore suppress an amount of variation caused by temperature influence of the intensity of the light passing through the measurement cell 5, shown in FIG. 1 below, during the sample measurement and the intensity of the light passing through the dimming element 6 during the reference measurement.

The light detector is a multi-channel detector, and the amplifier is preferably configured to amplify the analog sample light intensity signal and the analog reference light intensity signal outputted from different channels of the multi-channel detector with mutually different amplification factors. This can increase the sample light intensity signal for each wavelength point (each channel) to such a degree that does not exceed the full scale of the A/D converter.

In conventional spectroscopic analysis, absorbance reference (an absorbance of zero) is set by using air, but air cannot be used to provide the absorbance reference in the present invention. This is because, in the case where the amplification factor of the amplifier is set as described above, the light intensity signal obtained when the air is stored in the measurement cell exceeds the full scale of the A/D converter and goes off the scale as a result of being subjected to A/D conversion by the A/D converter. Thus, in the present invention, the absorbance reference is set by using a reference liquid. More specifically, a light intensity signal obtained in the case where the reference liquid is stored in the measurement cell is provided for absorbance reference (an absorbance of zero). The absorbance in the case where this reference liquid is provided for the absorbance reference is expressed by the following equation.

[Equation 4]

$$\mathrm{Abs}(\lambda i) = \log \frac{I_R(\lambda i)}{I_S(\lambda i)} + k(\lambda i) \qquad \text{(Equation 4)}$$

where $k(\lambda i)$ is a correction value for setting the absorbance at zero during reference liquid measurement, and is expressed by the following equation. $I_{reference\ liquid}(\lambda i)$ is a sample light intensity during the reference liquid measurement.

[Equation 5]

$$k(\lambda i) = -\log \frac{I_R(\lambda i)}{I_{reference\ liquid}(\lambda i)} \quad \text{(Equation 5)}$$

Advantageous Effects of Invention

The present invention with the configuration as described above can improve an S/N ratio and also improve light intensity resolution provided by an AD converter.

DETAILED DESCRIPTION OF PREFERRED EMBODIMENT

Hereinafter, a spectroscopic analyzer according to the present invention will be described with reference to the accompanying drawings.

The spectroscopic analyzer 100 of the present embodiment is provided, for example, in a manner such as to lie in a chemical solution pipe that supplies a chemical solution such as hydrofluoric acid and is provided in a semiconductor manufacturing device, and measures, for example, concentration of this chemical solution (liquid sample) such as the hydrofluoric acid by using a spectroscopic analysis method. The concentration obtained in this manner is used to control, for example, the concentration of the chemical solution.

Figure 1:
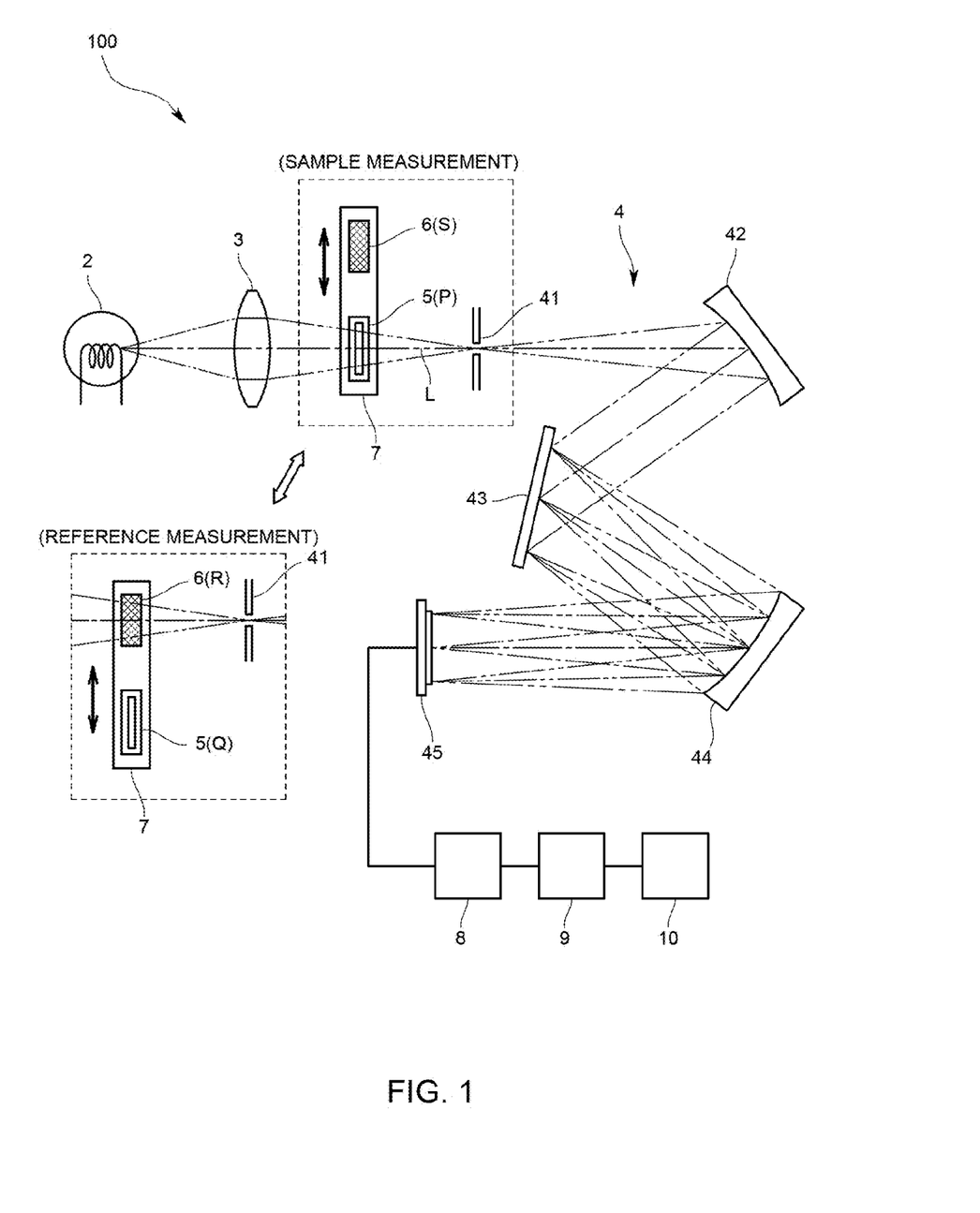
FIG. 1 is a schematic diagram showing a configuration of a spectroscopic analyzer according to an embodiment of the present invention.

More specifically, the spectroscopic analyzer 100 includes: as shown in FIG. 1, a light source 2; a condensing optical system 3 which condenses light exiting from the light source 2; a light detection unit 4 which is provided on a light path L of the light condensed by the condensing optical system 3 and which detects this light; a measurement cell 5 which is movable on the light path L between the condensing optical system 3 and the light detection unit 4; a dimming element 6 which is similarly movable on the light path L between the condensing optical system 3 and the light detection unit 4; a movement mechanism 7 which moves the measurement cell 5 and the dimming element 6; an amplifier 8 which amplifies analog light intensity signals outputted from the light detection unit 4; an A/D converter 9 which converts the analog light intensity signals into digital light intensity signals; and an arithmetic device 10 which calculates absorbance and concentration by using a digital sample light intensity signal outputted from the A/D converter 9 during sample measurement and a digital reference light intensity signal outputted from the A/D converter 9 during reference measurement.

The light source 2 is a continuous light source formed of, for example, a halogen lamp.

The condensing optical system 3 is provided in a direction in which the light source 2 emits light, condenses the light emitted from the light source 2, and is formed by using a condensing lens in the present embodiment.

The light detection unit 4 divides the light condensed by the condensing optical system 3 into different wavelengths and performs detection for each of their wavelength components. More specifically, the light detection unit 4 includes: an entrance slit 41 provided near a focal position of the light of the condensing optical system 3; a concave mirror 42 which turns light entering from the entrance slit 41 into a parallel beam; a diffraction grating 43 which receives the parallel beam from the concave mirror 42 and divides it into different wavelengths; a concave mirror 44 which condenses light of each of the wavelengths divided by the diffraction grating 43; and a multi-channel detector 45 which detects the light of each wavelength condensed by the concave mirror 44. The multi-channel detector 45 detects light in a near-infrared region. Alternatively, it may have a light detector for detecting light in an ultraviolet region.

A light intensity signal outputted from the multi-channel detector 45 is amplified by the amplifier 8, and the analog signal is converted into the digital signal by the A/D converter 9. Then the light intensity signal (optical spectrum data) outputted from the A/D converter 9 is inputted to the arithmetic device 10, which calculates an absorbance spectrum of the chemical solution based on an optical spectrum obtained by the light detection unit 4 and a reference spectrum previously obtained through calibration, and using this absorbance spectrum, concentration of a component contained in the liquid sample is calculated.

The measurement cell 5 is, for example, a flow cell provided in a circulation path formed by a chemical solution pipe connected to a chemical solution tank of a semiconductor wet station. This measurement cell 5 can be moved by the movement mechanism 7 to be described below between a measurement position P located on the light path L between the condensing optical system 3 and the light detection unit 4 (position during sample measurement) and a withdrawal position Q withdrawn from the aforementioned measurement position P.

The dimming element 6 is used for the reference measurement, and has a lower transmittance than that of optical glass (approximately 90%), and this transmittance is equal in degree to a transmittance of the liquid sample stored in the measurement cell 5 in the present embodiment. That is, the transmittance of the dimming element 6 is set so that either of a reference light intensity and a sample light intensity becomes less than or equal to ten times the other one of the reference light intensity and the sample light intensity. In the present embodiment, the transmittance of the liquid sample is approximately 1 to 10%, and the transmittance of the dimming element 6 is 10%. Moreover, the dimming element has water as its component or is an optical filter. The one having water as its component requires temperature correction, while the optical filter does not necessarily require temperature correction since its temperature change is minor, and therefore it is desirable to use the optical filter.

This equalizes intensity of light passing through the measurement cell 5 in the sample measurement and intensity of light passing through the dimming element 6 in the reference measurement, which can equalize the light intensity signal outputted from the multi-channel detector 45. Moreover, the dimming element 6 can be moved by the movement mechanism 7 to be described below between the reference position R (position in the reference measurement) located on the light path L between the condensing optical system 3 and the light detection unit 4 and the withdrawal position S withdrawn from this reference position R.

At least just in front or just behind of the dimming element 6, optical glass may be arranged, and considering optical effect of, for example, a refractive index of the dimming element 6, a light beam in the reference measurement may be brought into agreement with a light beam in the sample measurement.

The movement mechanism 7 moves the measurement cell 5 and the dimming element 6, and selectively locates the measurement cell 5 at the measurement position P or the dimming element 6 at the reference position R. The measurement cell 5 and the dimming element 6 of the present embodiment are so integrated as to be parallel to the light path L of the light condensed by the condensing optical system 3, and the movement mechanism 7 causes integral, advancing and retreating movement of the measurement cell 5 and the dimming element 6 in a direction orthogonal to the light path L. The movement mechanism 7 includes, although not shown, for example, a driving motor and a rack and pinion mechanism which converts a rotational motion of a driving shaft of this motor into a translational motion.

However, in the spectroscopic analyzer 100 of the present embodiment, an amplification factor of the amplifier 8 is set so that a reference light intensity signal obtained during the reference measurement and the sample light intensity signal obtained during the sample measurement become less than or equal to a full scale of the A/D converter 9. That is, the amplification factor of the amplifier 8 is equal between the reference measurement and the sample measurement, and the amplification factor of the amplifier 8 is set so that both the reference light intensity signal and the sample light intensity signal become less than or equal to the full scale of the A/D converter 9 and become as large as possible without exceeding the aforementioned full scale. Moreover, the amplification factor of the amplifier 8 is a value with which an output value of the A/D converter 9 exceeds the full scale and goes off the scale in a case of passage through the air or a conventional glass plate without going through the dimming element 6 in the reference measurement. The amplification factor of the amplifier 8 may be a fixed value set before the measurement, for example, at time of manufacturing or shipment, or may be, for example, a variable value which can be changed every measurement.

Figure 3:
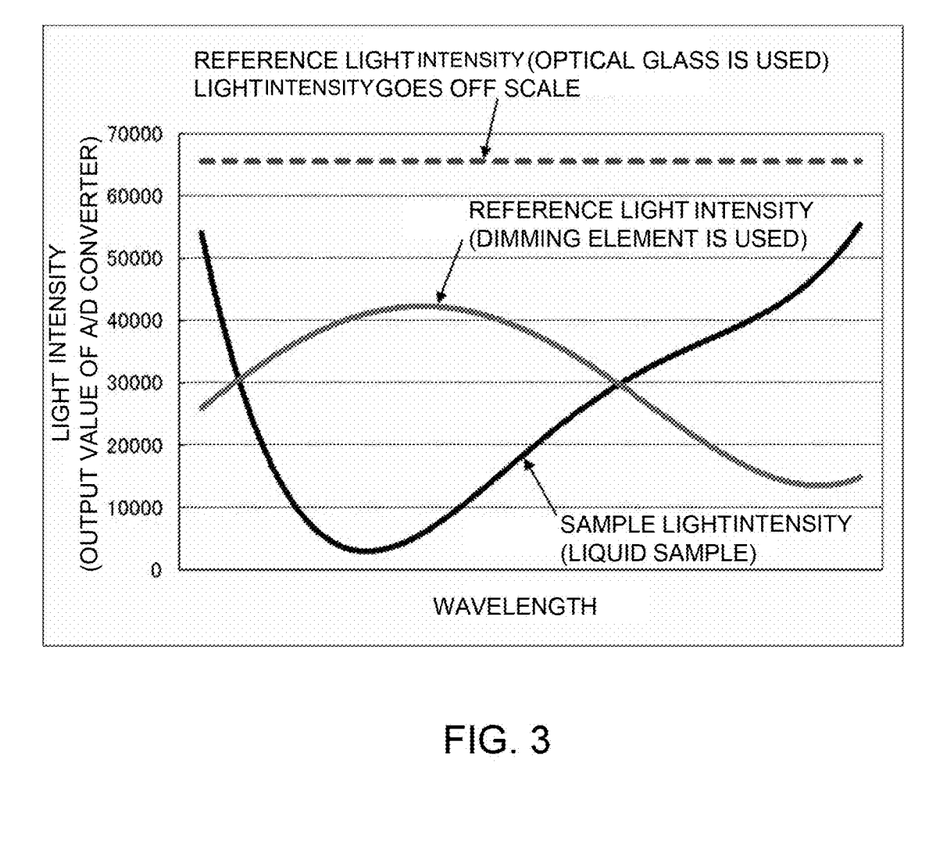
FIG. 3 is a diagram showing light intensity signals obtained by an A/D converter in the spectroscopic analyzer of the present embodiment.

FIGS. 2 and 3 show output values in the case where a 16-bit A/D converter, that is, an A/D converter with a full scale of 65,535 is used. FIG. 2 shows the output values of the A/D converter in a conventional spectroscopic analyzer, and FIG. 3 shows the output values of the A/D converter 9 in the spectroscopic analyzer 100 of the present embodiment. While the output value of the sample light intensity signal is several hundreds to several thousands in the conventional device (see FIG. 2), the output value of the sample light intensity signal is several thousands to several tens of thousands in the device of the present embodiment, which is an increase of about one order of magnitude. That is, this means that the sample light intensity per bit in the A/D converter 9 can be obtained with small resolution, which can improve light intensity resolution of the A/D converter 9. In the case where optical glass is used without using the dimming element 6 in the reference measurement, the reference light intensity signal goes off the scale (see FIG. 3).

Moreover, absorbance reference (an absorbance of zero) in this spectroscopic analyzer 100 is not set by storing air in the measurement cell 5 but is set by storing reference liquid (for example, water) in the measurement cell 5.

Figure 4:
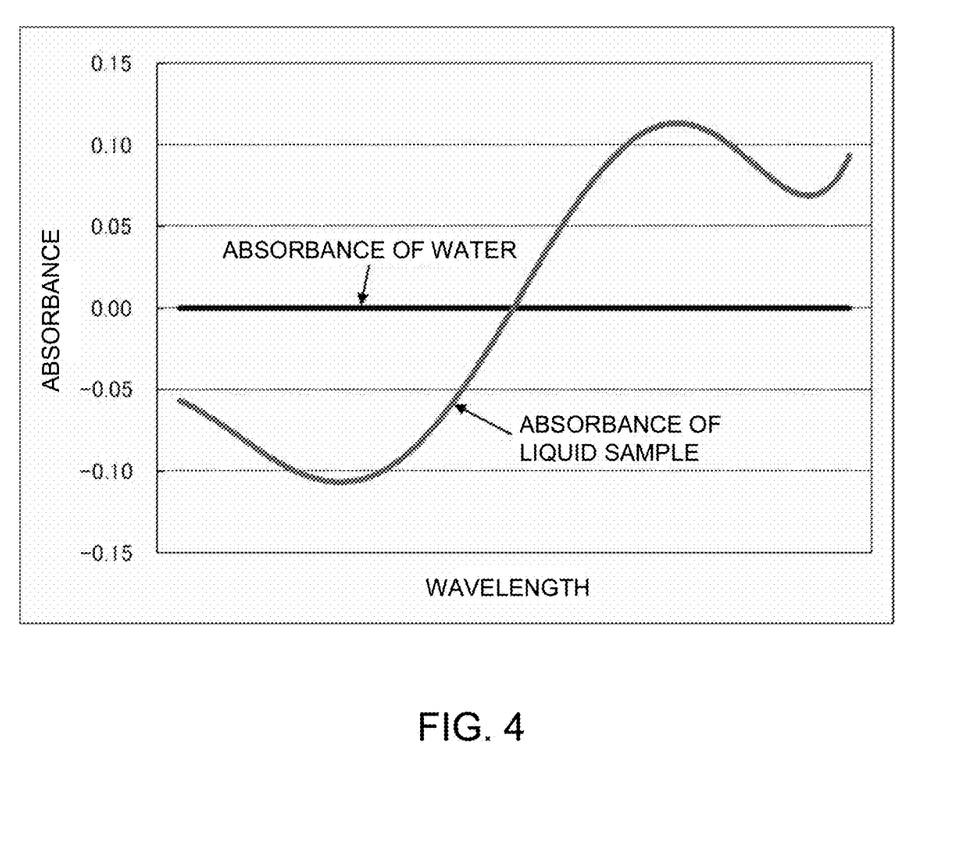
FIG. 4 is a diagram showing absorbance of a liquid sample in the case where absorbance of a reference liquid (water) is zero.

FIG. 4 shows an example of measurement of absorbance spectrums of the reference liquid and a liquid sample in the case where the reference liquid is provided for absorbance reference. The absorbance spectrums are equal to those in a conventional case where air is provided for the absorbance reference.

Figure 5:
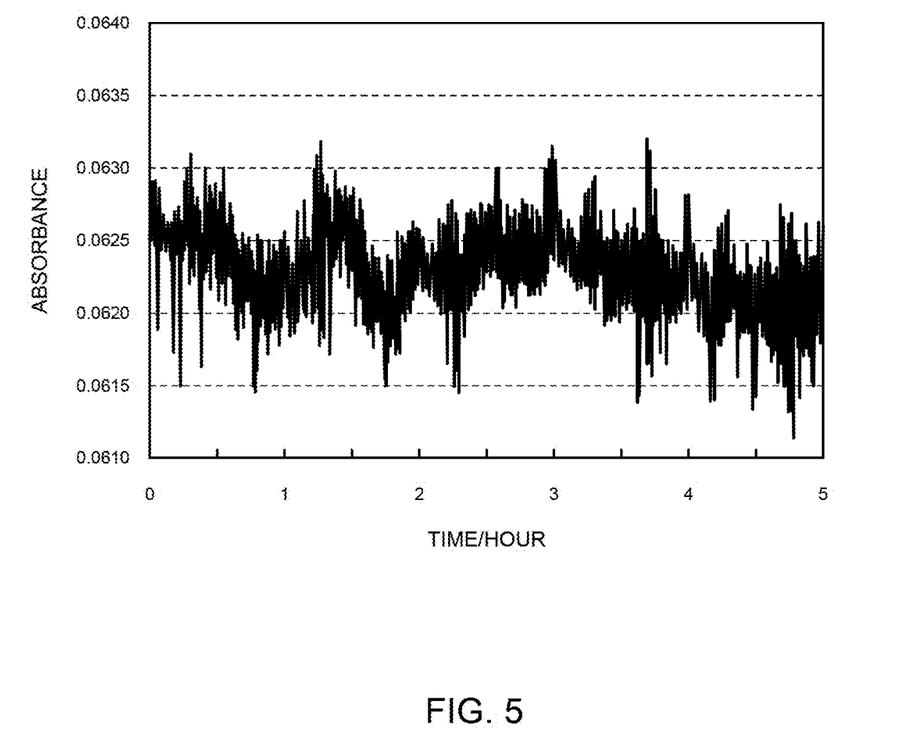
FIG. 5 is a diagram showing absorbance stability in the conventional spectroscopic analyzer.
Figure 6:
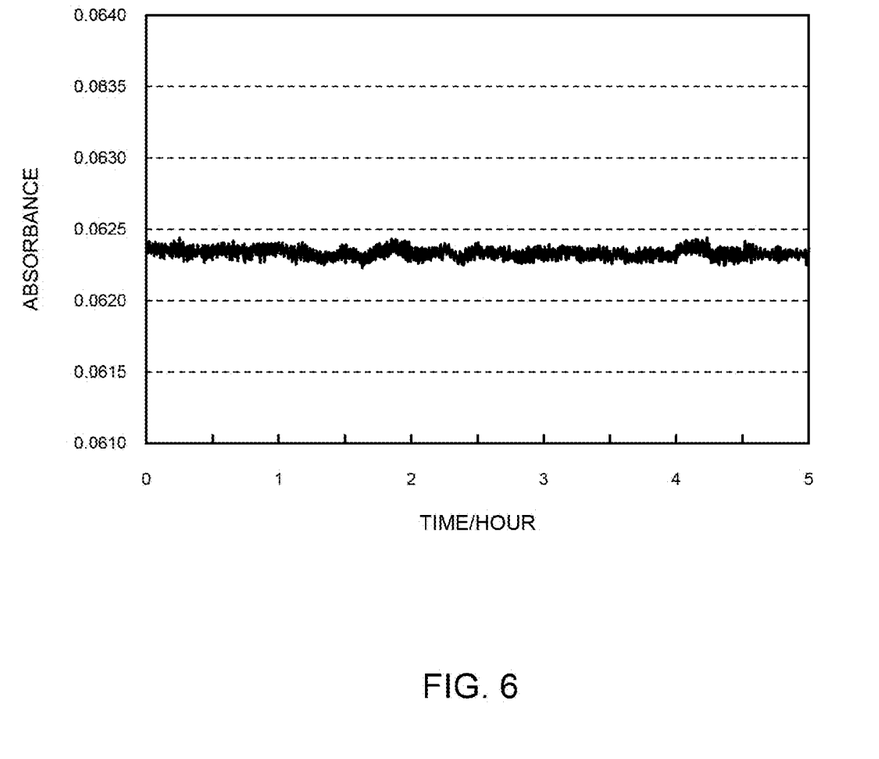
FIG. 6 is a diagram showing absorbance stability in the spectroscopic analyzer of the present embodiment.

Next, FIGS. 5 and 6 show temporal variation in absorbance with a predetermined wavelength in the case where concentration of the liquid sample is constant. FIG. 5 is a diagram showing the temporal variation in the absorbance in the conventional spectroscopic analyzer, and FIG. 6 is a diagram showing the temporal variation in the absorbance in the spectroscopic analyzer 100 of the present embodiment.

As shown in FIG. 5, the conventional spectroscopic analyzer has a large absorbance variation width and has an unstable measurement system. On the other hand, as shown in FIG. 6, the spectroscopic analyzer 100 of the present embodiment has a remarkably small absorbance variation width, proving that it has excellent absorbance stability.

Figure 7:
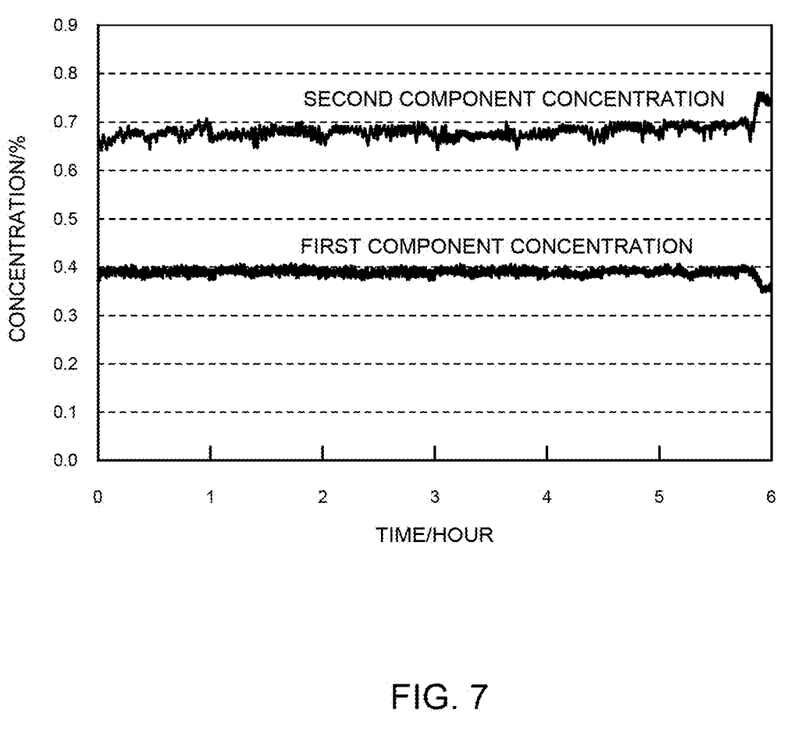
FIG. 7 is a diagram showing concentration stability in the conventional spectroscopic analyzer.
Figure 8:
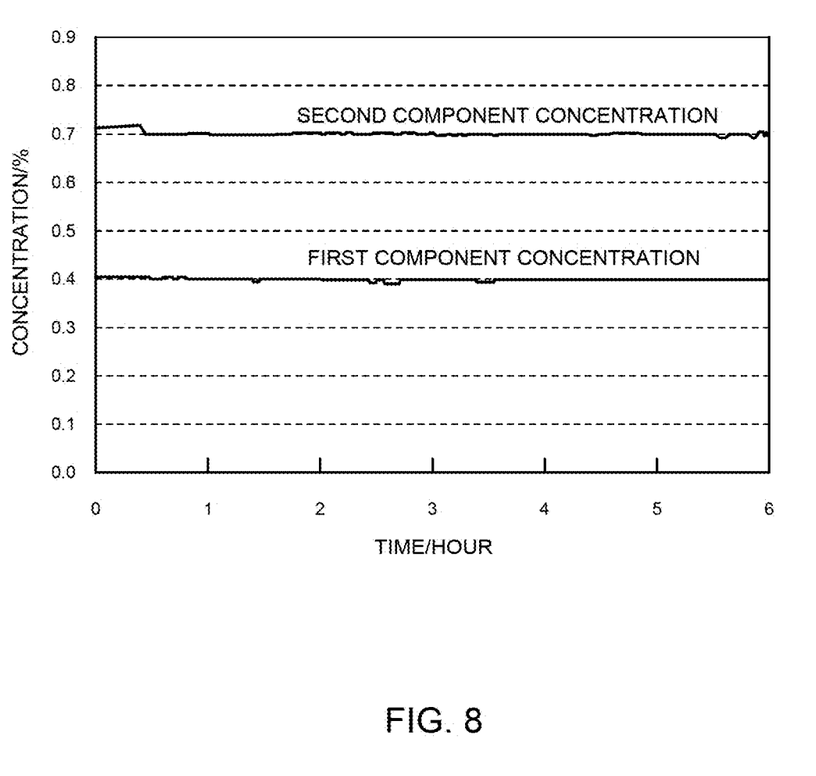
FIG. 8 is a diagram showing concentration stability in the spectroscopic analyzer of the present embodiment.

Moreover, by substituting the absorbance in the aforementioned equation (1), concentration of each component contained in the liquid sample can be calculated. Here, FIGS. 7 and 8 show temporal variations in concentration where the concentration of the liquid sample is constant. In FIGS. 7 and 8, the liquid sample is an ammonia-hydrogen peroxide solution, a first concentration component is ammonia, and a second concentration component is hydrogen peroxide. FIG. 7 is a diagram showing the temporal variation in the concentration in the conventional spectroscopic analyzer, and FIG. 8 is a diagram showing the temporal variation in the concentration in the spectroscopic analyzer 100 of the present embodiment.

As shown in FIG. 7, variation of the measured concentration of the conventional spectroscopic analyzer denotes unsteadiness of the measurement system. On the other hand, as shown in FIG. 8, the spectroscopic analyzer 100 of the present embodiment has a small concentration variation width, proving that it has excellent concentration stability.

With the spectroscopic analyzer 100 according to the present embodiment configured as described above, the transmittance of the dimming element 6 is equalized with the transmittance of the liquid sample, which can therefore intentionally reduce the light intensity signal of the light that has passed through the dimming element 6 during the reference measurement to thereby equalize it with the light intensity signal of the light that has passed through the measurement cell 5 during the sample measurement.

Then the amplification factor of the amplifier 8 is set so that the reference light intensity signal and the sample light intensity signal become less than or equal to the full scale of the A/D converter 9, which can therefore increase the reference light intensity signal and the sample light intensity signal to such degrees that do not exceed the full scale of the A/D converter 9.

Therefore, the light intensity signal obtained during the sample measurement is amplified by the amplifier 8 (since an output voltage is increased by increasing output resistance of the light detector 45), which can therefore improve an S/N ratio for disturbance noise such as electromagnetic noise. Moreover, the sample light intensity signal can enlarged with respect to the full scale of the A/D converter 9, which can therefore improve the light intensity resolution in the A/D converter 9. As a result of the above, accurate light intensity measurement is possible, permitting concentration measurement with high accuracy.

Note that the present invention is not limited to the embodiment described above.

For example, in the embodiment described above, the amplification ratio of the amplifier provided at a later stage than the light detector is adjusted to thereby set the sample light intensity signal and the reference light intensity signal to be less than or equal to the full scale of the A/D converter and also be as large as possible, but a maximum possible number of light intensity signals (voltage values) outputted from the light detector can be provided. That is, the light intensity signal can be increased by increasing a resistance value of an output resistor provided at the light detector (for example, approximately ten times that of the conventional one).

Moreover, in the embodiment described above, the measurement cell 5 and the dimming element 6 are moved to make switching between the sample measurement and the reference measurement possible, but the measurement cell 5 and the dimming element 6 may be fixed while the measurement optical system including, for example, the light source 2 and the light detection unit 4 may be moved. Moreover, both the measurement cell 5 and the dimming element 6 and the measurement optical system may be moved.

The amplifier of the embodiment described above may be provided for each different channel of the multi-channel detector 45 to thereby provide a configuration such that the light intensity signals outputted from the different channels of the multi-channel detector 45 are amplified with the same amplification factor or a configuration such that the light intensity signals outputted from the different channels may be amplified with mutually different amplification factors. This can increase the sample light intensity signal for each wavelength point (each channel) to such a degree that does not exceed the full scale of the A/D converter.

In the embodiment described above, the spectroscopic analyzer which analyzes a liquid sample has been described, but a spectroscopic analyzer which analyzes a gaseous sample may also be applied.

Needless to say, the present invention is not limited to the embodiment described above, and various modifications can be made thereto within a range not departing from the spirits of the present invention.

REFERENCE CHARACTERS LIST

100 Spectroscopic analyzer
2 Light source
45 Multi-channel detector (light detector)
5 Measurement cell
6 Dimming element
8 Amplifier
9 A/D converter
10 Arithmetic device

The invention claimed is:

1. A spectroscopic analyzer comprising:
a light source;
a measurement cell storing a liquid sample irradiated with light of the light source during sample measurement;
a dimmer being irradiated with the light of the light source during reference measurement, and transmitting a part of the light;
a light detector configured to detect sample light which has passed through the measurement cell during sample measurement and configured to detect reference light which has passed through the dimmer during reference measurement;
an amplifier configured to amplify an analog sample light intensity signal outputted from the light detector during sample measurement and configured to amplify an analog reference light intensity signal outputted from the light detector during reference measurement;
an A/D converter configured to convert the analog sample light intensity signal into a digital sample light intensity signal and to configured amplify the analog reference light intensity signal into a digital reference light intensity signal; and
a processor configured to calculate an absorbance of the liquid sample using the digital sample light intensity signal outputted from the A/D converter during the sample measurement and by using the digital reference light intensity signal outputted from the A/D converter during the reference measurement, wherein
the dimmer has lower transmittance than that of optical glass, the dimmer having water as its component or being an optical filter; and
the analog sample light intensity signal and analog reference light intensity signal inputted to the A/D converter are amplified in a manner such that the digital reference light intensity signal and the digital sample light intensity signal become less than or equal to a full scale of the A/D converter.

2. The spectroscopic analyzer according to claim 1, wherein
the light detector is a multi-channel detector, and
the amplifier is configured to be capable of amplifying the analog sample light intensity signal and the analog reference light intensity signal outputted from different channels of the multi-channel detector with mutually different amplification factors.

3. A spectroscopic analysis method of:
arranging, between a light source and a light detector, a measurement cell storing a liquid sample to acquire an analog sample light intensity signal in sample measurement, arranging a dimmer to acquire an analog reference light intensity signal, and calculating absorbance by using a digital sample light intensity signal and a digital reference light intensity signal in reference measurement, the dimmer transmitting a part of the light, wherein
the digital sample light intensity signal and the digital reference light intensity signal are obtained by amplifying, by use of an amplifier, an analog sample light intensity signal of sample light and an analog reference light intensity signal of reference light detected by the light detector and converting the analog sample light intensity signal and the analog reference light signal into a digital sample light intensity signal and a digital reference light intensity signal by an A/D converter;
the dimmer has lower transmittance than that of optical glass, the dimmer having water as its component or being an optical filter; and
the analog sample light intensity signal and the analog reference light intensity signal inputted to the A/D converter are amplified in a manner such that the analog reference light intensity signal and the analog sample light intensity signal become less than or equal to a full scale of the A/D converter.

* * * * *